United States Patent
LaColla

(10) Patent No.: US 11,707,307 B2
(45) Date of Patent: Jul. 25, 2023

(54) SYSTEMS AND METHODS FOR TREATING RIB FRACTURES AND OSTEOTOMIES USING IMPLANTATION

(71) Applicant: GLOBUS MEDICAL, INC., Audubon, PA (US)

(72) Inventor: John LaColla, West Chester, PA (US)

(73) Assignee: Globus Medical, Inc., Audubon, PA (US)

(*) Notice: Subject to any disclaimer, the term of this patent is extended or adjusted under 35 U.S.C. 154(b) by 0 days.

(21) Appl. No.: 17/112,134

(22) Filed: Dec. 4, 2020

(65) Prior Publication Data

US 2022/0175428 A1    Jun. 9, 2022

(51) Int. Cl.
*A61B 17/80* (2006.01)
*A61B 17/17* (2006.01)
*A61B 17/70* (2006.01)

(52) U.S. Cl.
CPC ...... *A61B 17/8076* (2013.01); *A61B 17/1728* (2013.01); *A61B 17/707* (2013.01)

(58) Field of Classification Search
CPC . A61B 17/1728; A61B 17/70; A61B 17/7001; A61B 17/7032; A61B 17/7034; A61B 17/7035; A61B 17/7044; A61B 17/7062; A61B 17/707; A61B 17/8076; A61B 17/8894
See application file for complete search history.

(56) References Cited

U.S. PATENT DOCUMENTS

| | | | |
|---|---|---|---|
| 2,439,995 | A | 4/1948 | Thrailkill |
| 5,545,164 | A | 8/1996 | Howland |
| 5,743,907 | A | 4/1998 | Asher et al. |
| 5,814,046 | A | 9/1998 | Hopf |
| 5,976,135 | A | 11/1999 | Sherman et al. |
| 5,993,449 | A * | 11/1999 | Schlapfer ........... A61B 17/7059 606/70 |
| 6,342,057 | B1 | 1/2002 | Brace et al. |
| 6,547,790 | B2 | 4/2003 | Harkey, III et al. |
| 6,565,569 | B1 | 5/2003 | Assaker et al. |
| 6,569,164 | B1 | 5/2003 | Assaker et al. |
| 6,585,738 | B1 | 7/2003 | Mangione et al. |
| 6,706,046 | B2 | 3/2004 | Orbay et al. |
| 6,730,090 | B2 | 5/2004 | Orbay et al. |
| 6,730,091 | B1 | 5/2004 | Pfefferle et al. |
| 6,881,215 | B2 | 4/2005 | Assaker et al. |
| 6,969,390 | B2 | 11/2005 | Michelson |
| 7,008,423 | B2 | 3/2006 | Assaker et al. |

(Continued)

FOREIGN PATENT DOCUMENTS

| | | |
|---|---|---|
| JP | 2000501005 A | 2/2000 |
| JP | 2007505684 A | 3/2007 |
| JP | 2007083039 A | 4/2007 |

*Primary Examiner* — Larry E Waggle, Jr.

(57) ABSTRACT

Systems and methods include solutions for fixation at the rib head for fractures and osteotomies adjacent to the rib head and transverse process. The disclosed rib plates, anchor systems, other implants, and instrumentation may also be applied to mid-rib fractures. The systems and methods may be used in the treatment of rib deformities, including the correction of rib hump deformity via thoracoplasty, as well as general corrections of chest and rib deformities. Systems and methods herein may be used in chest wall reconstructions due to trauma, cancer, or deformity.

20 Claims, 18 Drawing Sheets

(56) References Cited

U.S. PATENT DOCUMENTS

| | | | |
|---|---|---|---|
| 7,156,847 B2* | 1/2007 | Abramson | A61B 17/8076 |
| | | | 606/71 |
| 7,229,445 B2 | 6/2007 | Hayeck et al. | |
| 7,488,327 B2 | 2/2009 | Rathbun et al. | |
| 7,563,263 B2 | 7/2009 | Orbay et al. | |
| 7,572,282 B2 | 8/2009 | Boomer et al. | |
| 7,658,754 B2 | 2/2010 | Zhang, II et al. | |
| 7,763,029 B2 | 7/2010 | Rathbun et al. | |
| 7,909,848 B2* | 3/2011 | Patel | A61B 17/1757 |
| | | | 606/280 |
| 8,182,485 B1 | 5/2012 | Gonzalez-Hernandez | |
| 8,343,195 B2 | 1/2013 | Rathbun et al. | |
| 8,361,075 B2 | 1/2013 | Gonzalez-Hernandez | |
| 8,574,234 B2 | 11/2013 | Gonzalez-Hernandez | |
| 8,740,903 B2 | 6/2014 | Bottlang et al. | |
| 8,926,675 B2 | 1/2015 | Leung et al. | |
| 9,775,657 B2 | 10/2017 | Bernstein et al. | |
| 10,219,849 B2 | 3/2019 | Madjarov | |
| 10,463,410 B2 | 11/2019 | Goodwin, Jr. et al. | |
| 10,517,659 B2 | 12/2019 | Sixto et al. | |
| 10,660,680 B2 | 5/2020 | Imai | |
| 10,687,875 B2 | 6/2020 | Smits et al. | |
| 2009/0069812 A1 | 3/2009 | Gillard et al. | |
| 2014/0142638 A1 | 5/2014 | Goodwin et al. | |
| 2017/0189088 A1 | 7/2017 | Lin | |
| 2018/0325557 A1 | 11/2018 | Suddaby | |
| 2019/0046251 A1* | 2/2019 | Detweiler | A61B 17/865 |
| 2019/0262040 A1 | 8/2019 | Kono | |
| 2019/0380745 A1 | 12/2019 | Hammann et al. | |
| 2020/0000504 A1 | 1/2020 | Rabiner et al. | |

* cited by examiner

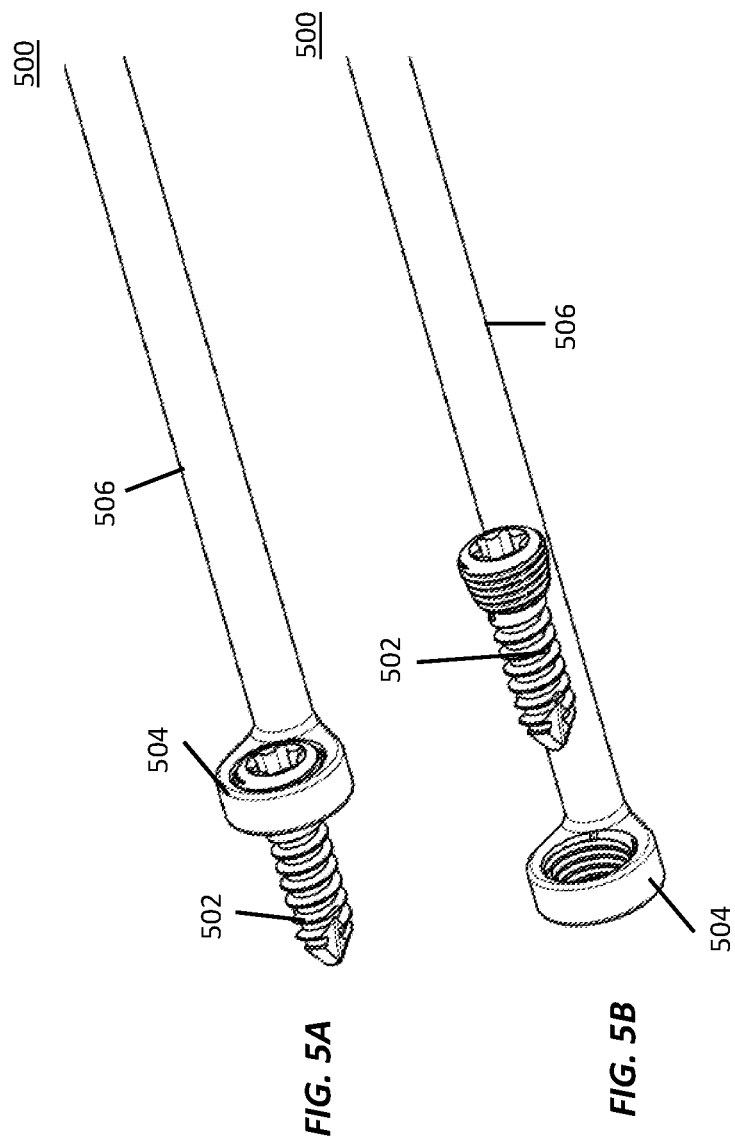

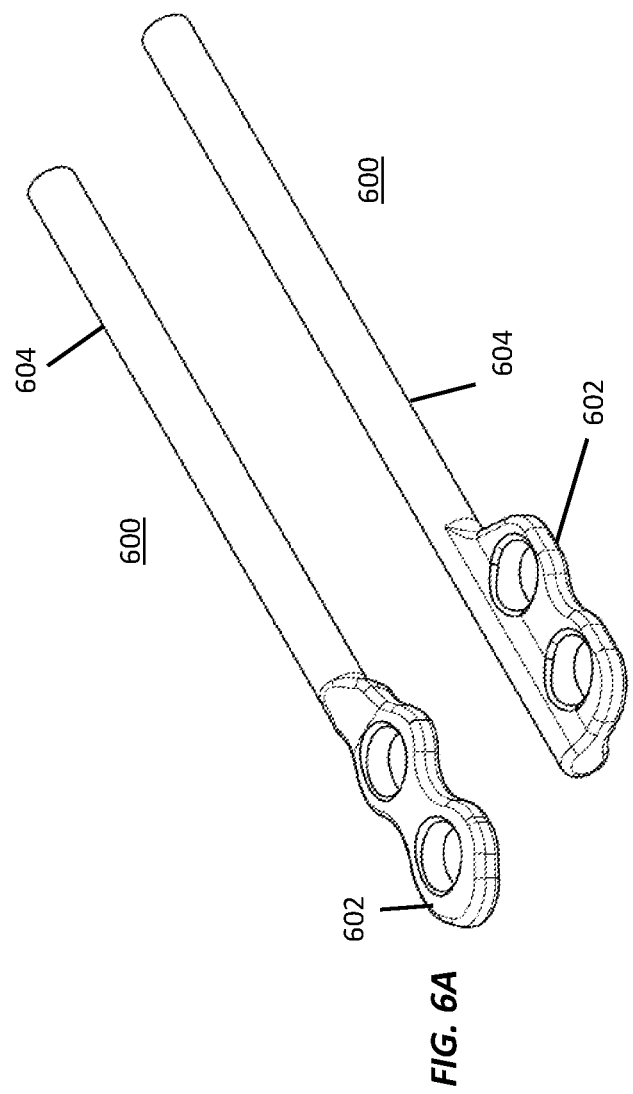

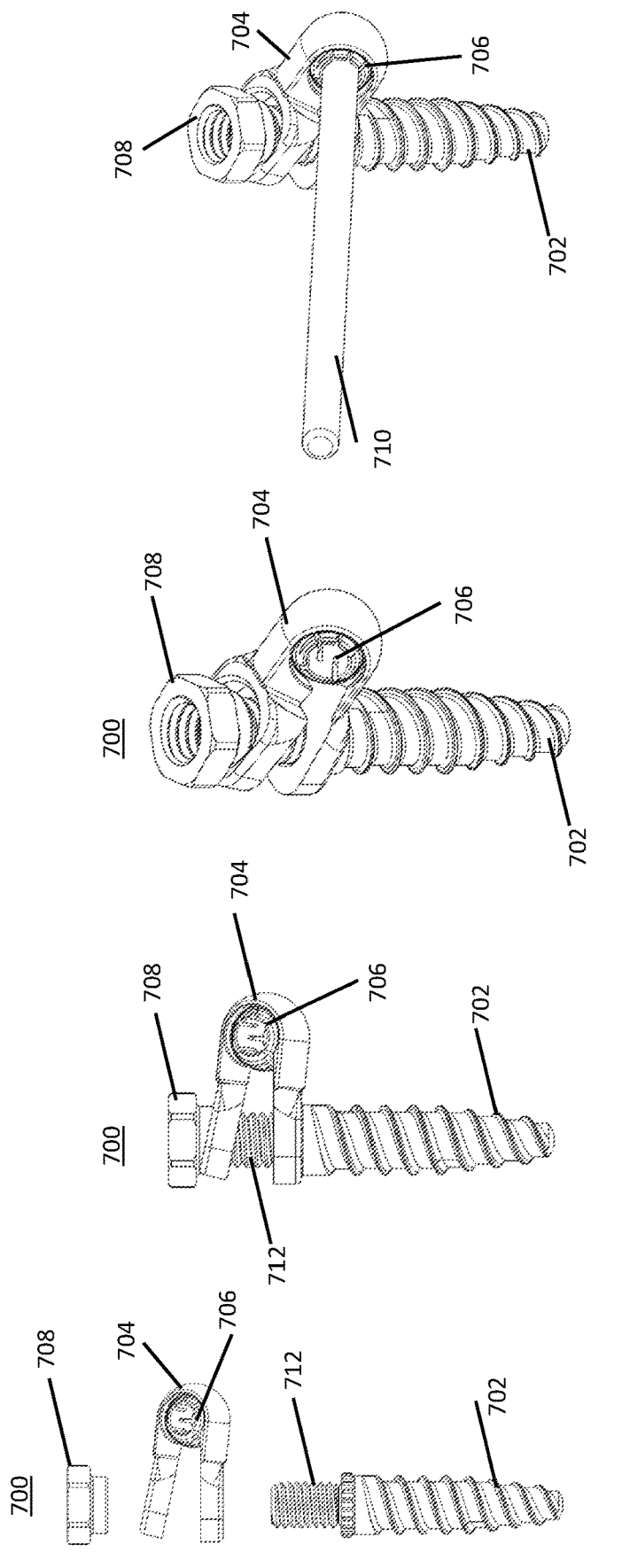

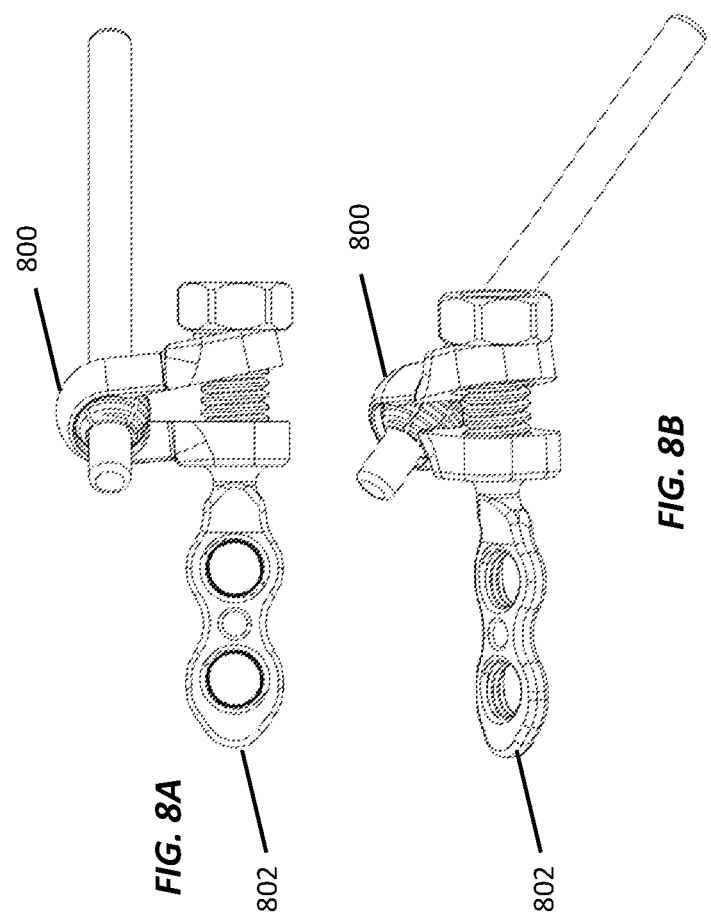

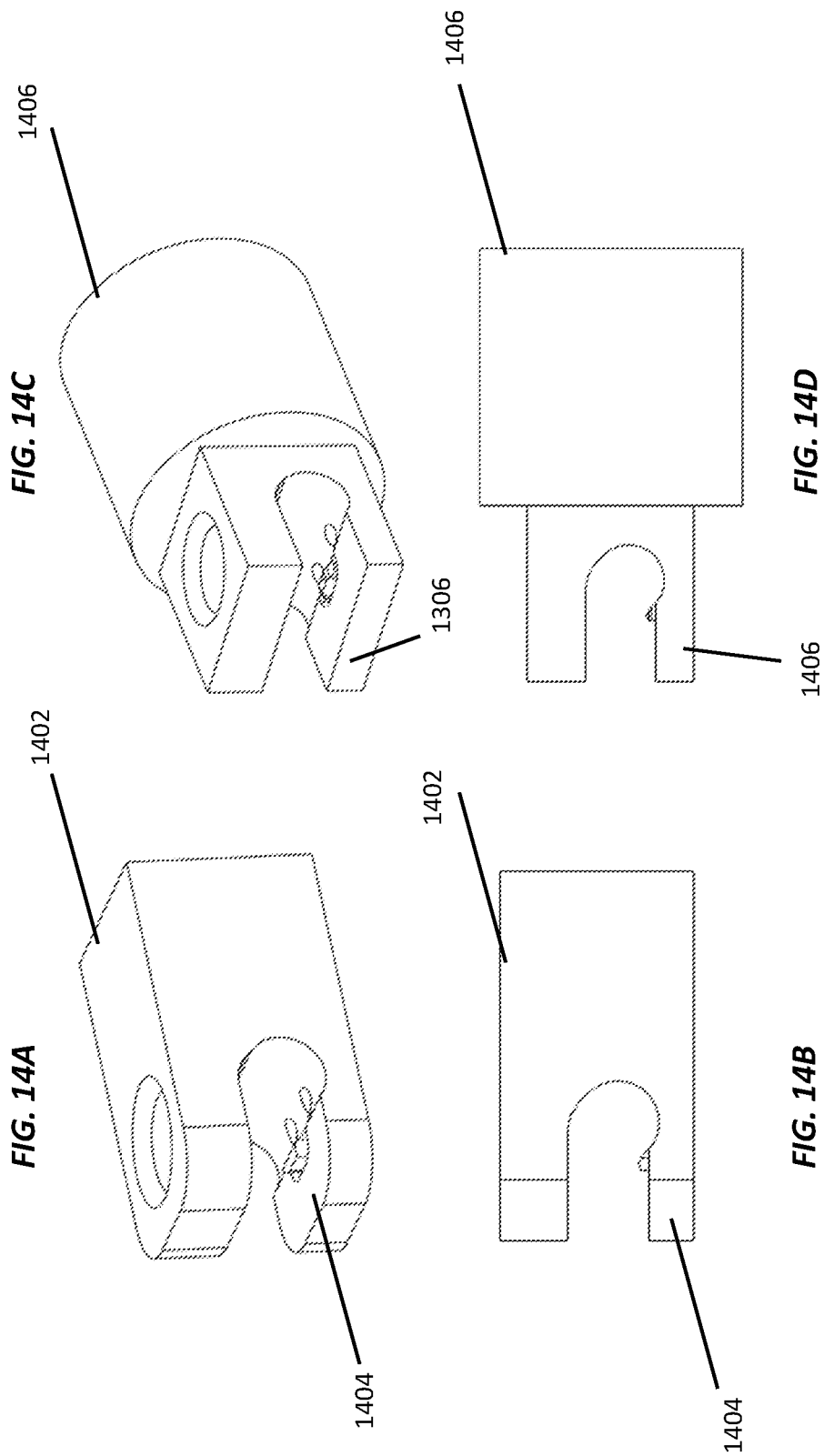

1408

1410

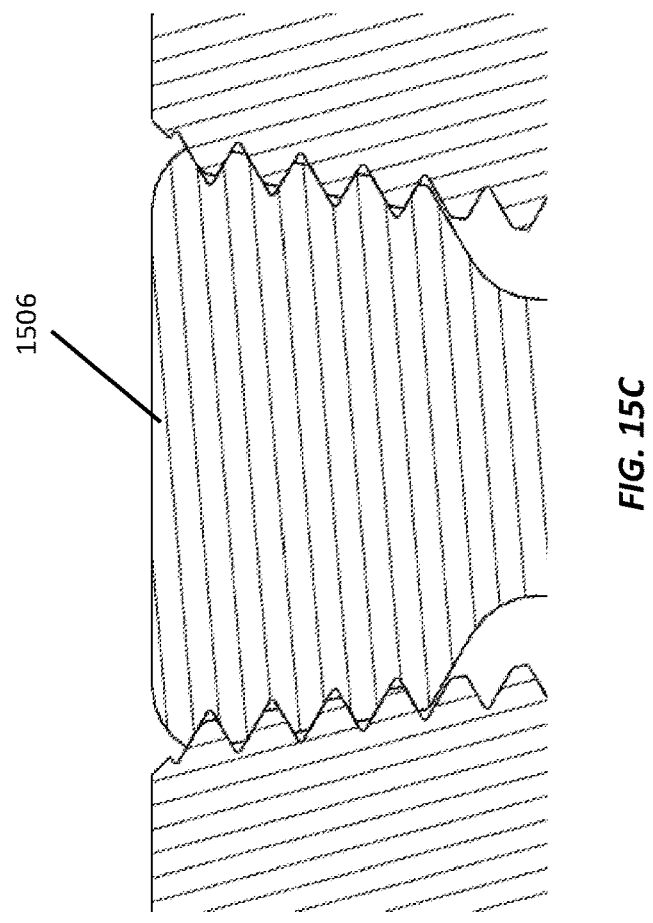
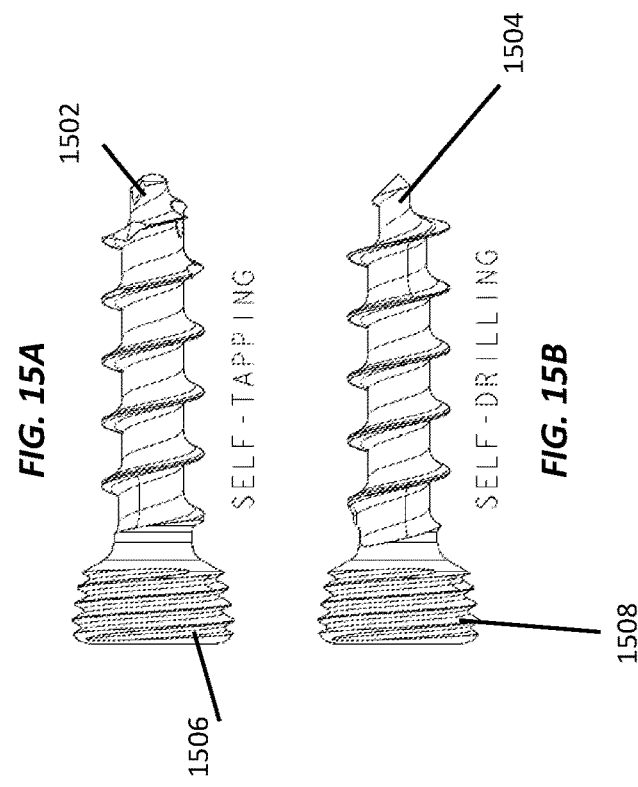
FIG. 15A
FIG. 15B
FIG. 15C

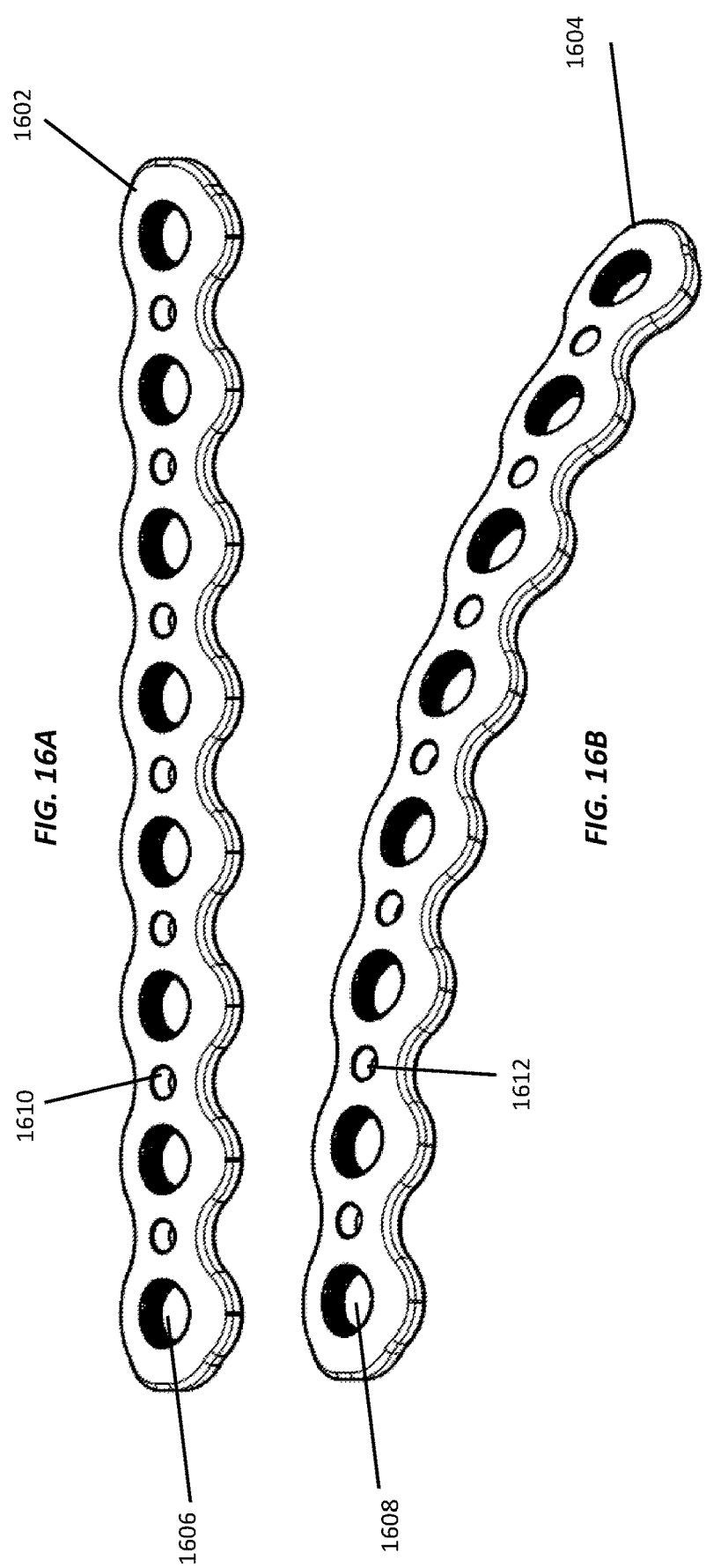

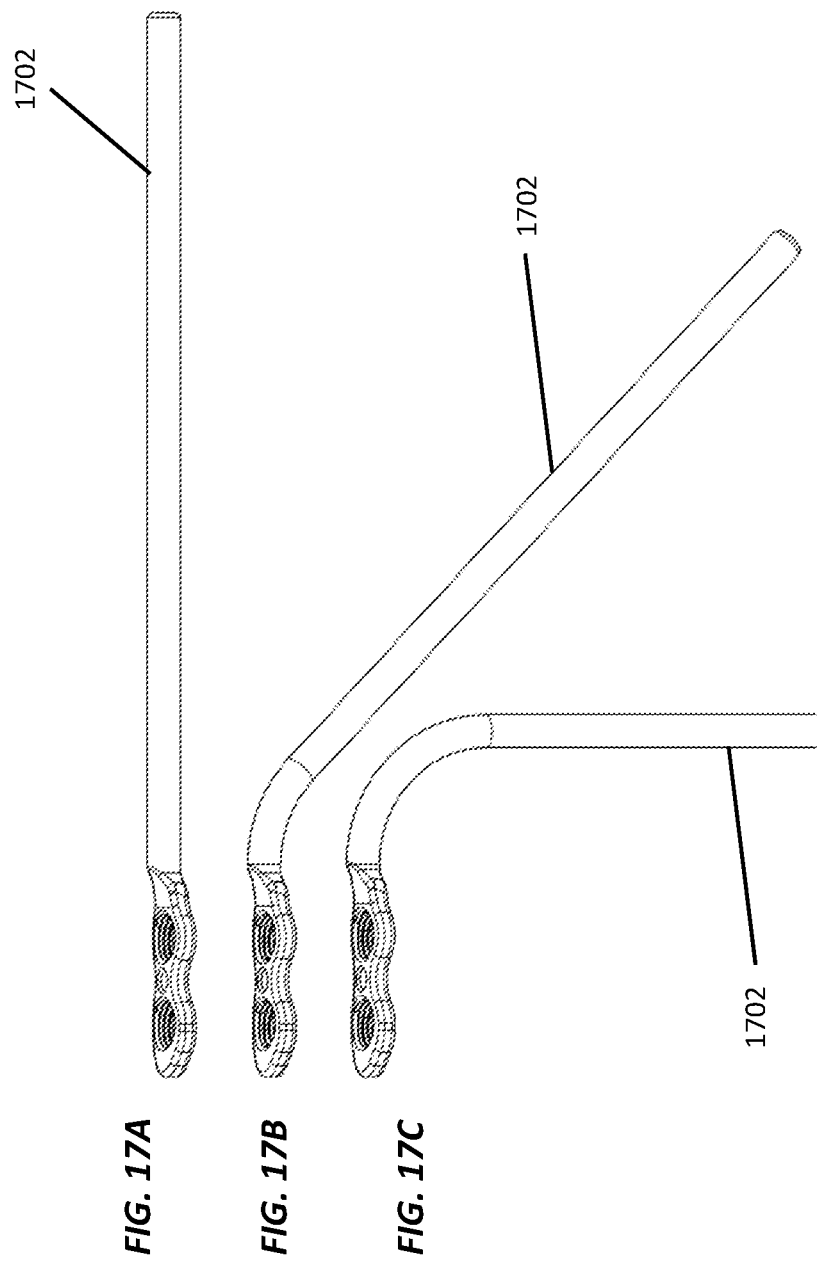

SYSTEMS AND METHODS FOR TREATING RIB FRACTURES AND OSTEOTOMIES USING IMPLANTATION

FIELD

The present disclosure relates to systems and devices for treating fractures and osteotomies of ribs. More particularly, the disclosure relates to implant assemblies for fixating the ribs to aid in the healing process.

BACKGROUND

Traditionally, fractures and osteotomies of the ribs were left untreated to heal, or were occasionally aided by casting. Some surgeons may have used sutures to reduce migration of the affected bone segments. More recently, rib fixation systems have become available, and early data and accounts suggest that the reduced motion and increased stability may reduce the pain associated with healing.

Current rib fixation devices are often plate-style, using screws or other anchors to fixate across a fracture site. These methods are sufficient for fractures and osteotomies which occur mid-rib and have adequate bone available on either side of the fracture for fixation, typically two (2) or three (3) screws on either side. In the case of posterior rib fractures adjacent to the rib head, the existing methods are inadequate due to lack of fixation.

What is needed are rib fixation solutions for fixation at the rib head, for fractures and osteotomies adjacent to the rib head and transverse process. What is also needed are fixation solutions that may be applied to mid-rib fractures, making them more versatile and capable of treating a wider range of pathologies than existing methods.

SUMMARY

According to one embodiment, a rib plate for treating a fracture of a rib bone. The rib plate includes a plate portion that contacts a surface of the rib bone to be treated, a first screw hole that receives a first screw to fixate the plate portion to the surface of the rib bone to be treated, an implant portion that receives a longitudinal member, and a fastener to secure the longitudinal member to the implant portion.

According to one embodiment, a rib plate system for treating a fracture of a rib bone. The rib plate system includes a rib plate that contacts a surface of the rib bone. The rib plate includes a plate portion that contacts a surface of the rib bone to be treated, a first screw hole, and an implant portion. The rib plate system also includes a first screw received in the first screw hole to fixate the rib plate to the rib bone, and a longitudinal member configured to attach to the implant portion.

BRIEF DESCRIPTION OF THE DRAWINGS

The accompanying drawings, which are incorporated herein and constitute part of this specification, illustrate the presently preferred embodiments of the disclosure, and, together with the general description given above and the detailed description given below, serve to explain the features of the disclosure. In the drawings:

FIGS. 5A and 5B illustrate an exemplary embodiment of a rib head anchor consistent with the principles of the present disclosure.

FIGS. 6A-6B illustrate an exemplary embodiment of splint plate consistent with the principles of the present disclosure.

FIGS. 7A-7C illustrate an exemplary embodiment of a rib head anchor consistent with the principles of the present disclosure.

FIG. 7D illustrates an exemplary embodiment of a rib head anchor with a longitudinal member attached therein consistent with the principles of the present disclosure.

FIGS. 8A and 8B illustrate an exemplary embodiment of a rib head anchor system consistent with the principles of the present disclosure.

FIGS. 14A-14H illustrate exemplary embodiments of a capture feature for a rib plate consistent with the principles of the present disclosure.

FIGS. 15A-15C illustrate an exemplary embodiment of locking screw for a rib plate consistent with the principles of the present disclosure.

FIGS. 16A and 16B illustrate exemplary embodiments of a rib plate consistent with the principles of the present disclosure.

FIGS. 17A-17C illustrate an exemplary embodiment of a splint plate consistent with the principles of the present disclosure.

DETAILED DESCRIPTION

Figure 1C:
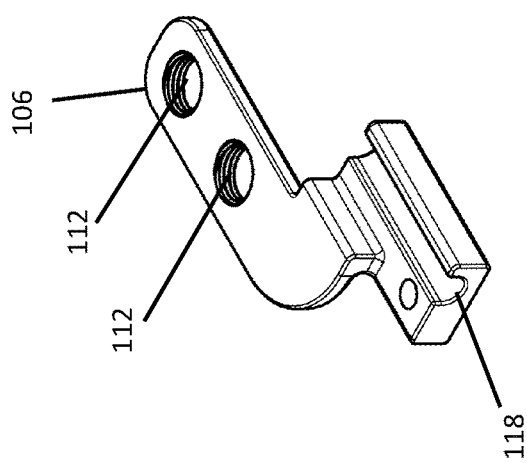
FIG. 1C illustrates an exemplary embodiment of a rib plate consistent with the principles of the present disclosure.

In the drawings, like numerals indicate like elements throughout, with alphabetical or prime identifiers indicating a particular one of the more generally identified element. Certain terminology is used herein for convenience only and is not to be taken as a limitation on the present invention. The following describes preferred embodiments of the present disclosure. However, it should be understood, based on this disclosure, that the invention is not limited by the preferred embodiments described herein.

Figure 1B:
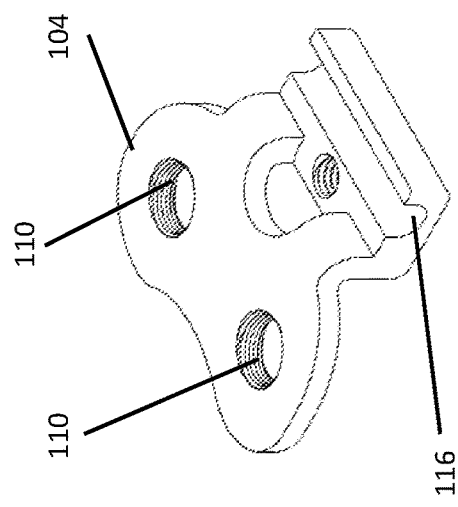
FIG. 1B illustrates an exemplary embodiment of a rib plate consistent with the principles of the present disclosure.
Figure 1A:
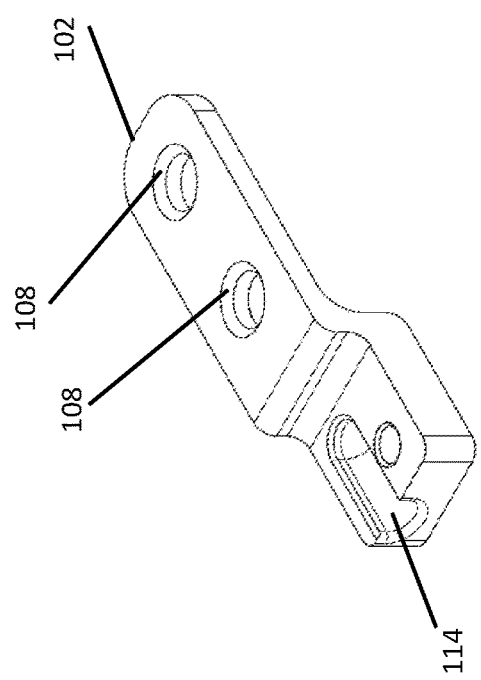
FIG. 1A illustrates an exemplary embodiment of a rib plate consistent with the principles of the present disclosure.

Referring now to FIG. 1A, illustrated is an exemplary embodiment of a rib plate 102 consistent with the principles of the present disclosure. FIGS. 1B and 1C illustrates other exemplary rib plates 104 and 106, respectively. Rib plate 102 may include screw holes 108 to fixate rib plate 102 to a surface of a rib using one or more screws or other anchors, such as sutures. Rib plate 102 may accept a longitudinal member from another implant at portion 114, which may be secured using various methods. The longitudinal member may be inserted in a top-loading manner to a top surface of the rib plate. Rib plate 102 may use a set screw to clamp the longitudinal member in place. Rib plate 110 may have screw holes 110 to accept screws or other anchors. Rib plate 106 may have screw holes 112 for this purpose. The varying geometry of the rib plates may be offset vertically and/or laterally to reduce profile/prominence, as well as to allow uninterrupted growth of the rib.

Figure 2:
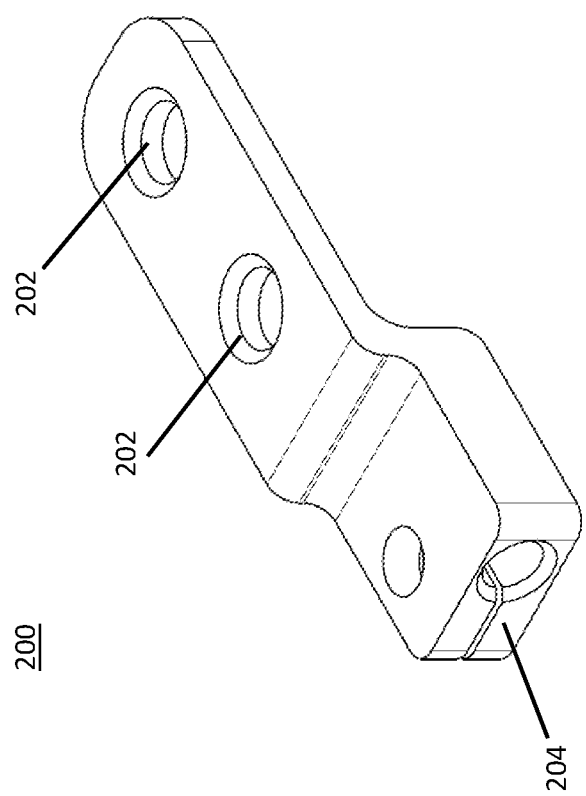
FIG. 2 illustrates an exemplary embodiment of a rib plate consistent with the principles of the present disclosure.

FIG. 2 illustrates a rib plate 200 consistent with the principles of the present disclosure. As with the rib plates of FIGS. 1A-1C, rib plate 200 may have screw holes 202 to fixate rib plate 200 to the surface of the rib, and similarly may be connected to a longitudinal member for stabilization of the fracture or osteotomy. Rib plate 200 has a clamp 204 that may receive the longitudinal member and be secured using a set screw.

Figure 3B:
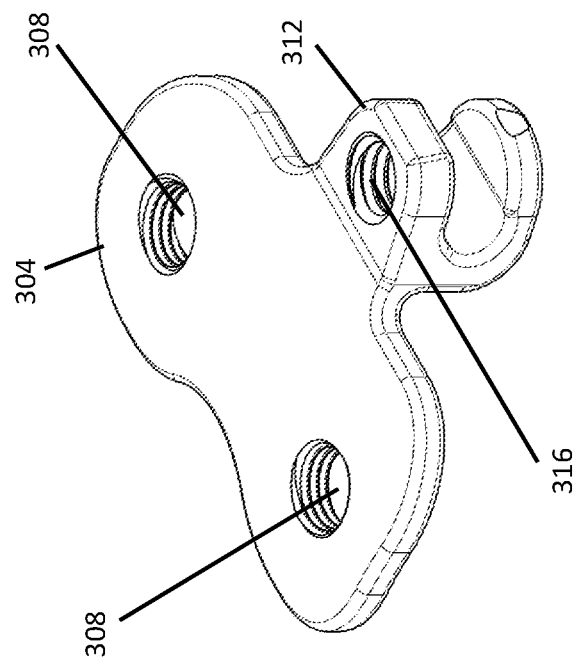
FIG. 3B illustrates an exemplary embodiment of a rib plate consistent with the principles of the present disclosure.
Figure 3A:
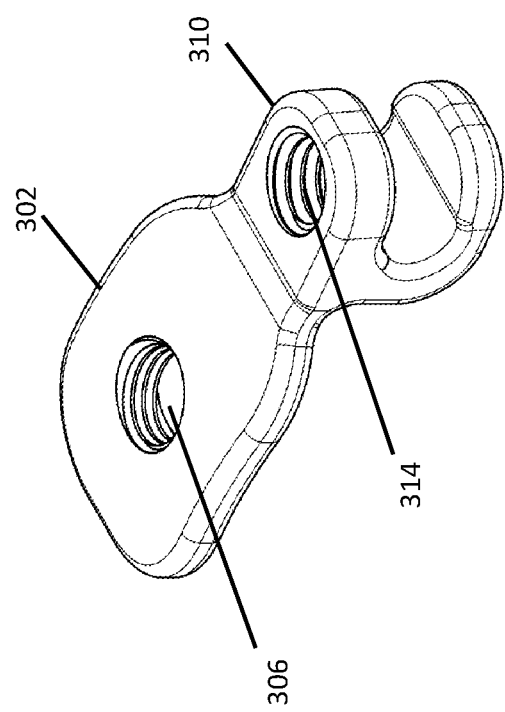
FIG. 3A illustrates an exemplary embodiment of a rib plate consistent with the principles of the present disclosure.
Figure 4C:
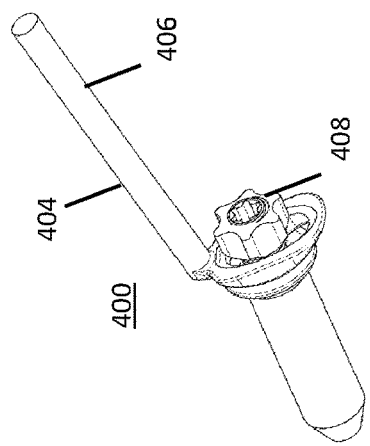
FIGS. 4A-4F illustrate an exemplary embodiment of a rib head anchor consistent with the principles of the present disclosure.
Figure 4F:
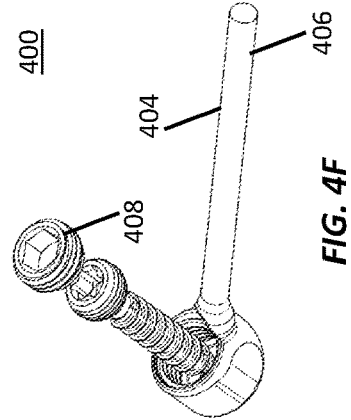
Figure 4B:
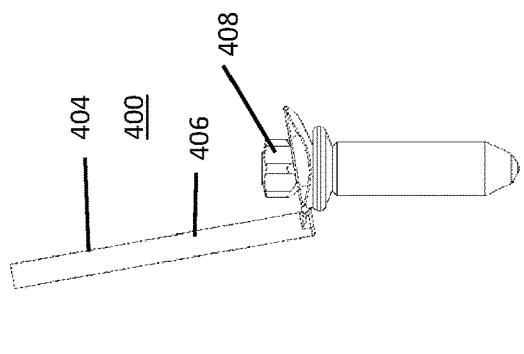
Figure 4E:
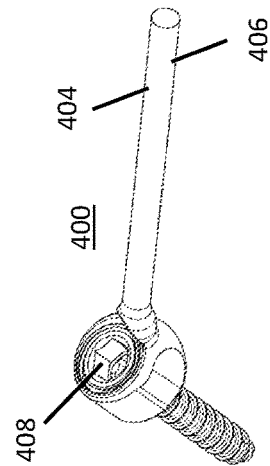
Figure 4A:
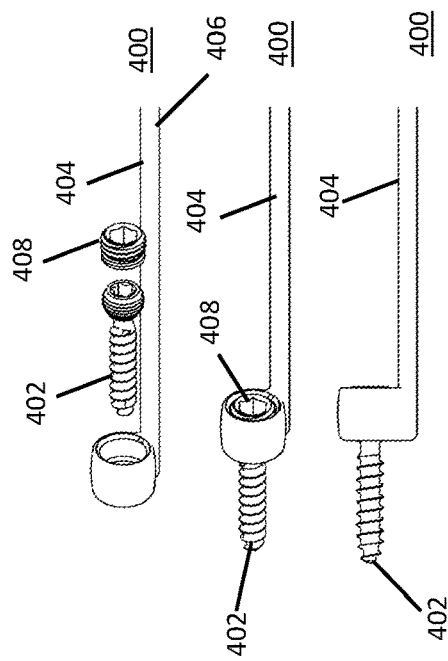
Figure 4D:
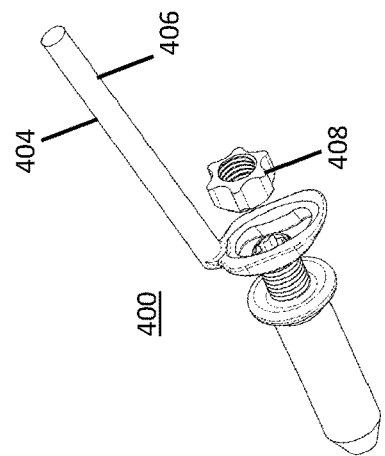

FIGS. 3A and 3B illustrates rib plates 302 and 304 consistent with the principles of the present disclosure. Rib plates 302 and 304 are similar to the other rib plates disclosed herein and fixate on the surface of the rib using screws and anchors received in screw holes 306 and 308, and connect to a longitudinal member via a clamp or locking mechanism 310, 312 offset from the rib, preferably either cephalad or caudal to the rib itself. Clamps 310 and 312 may be offset vertically relative to the plate portion to reduce prominence, and may be angled towards or away from the plate to facilitate access with instruments for tightening or other manipulation.

Figure 9B:
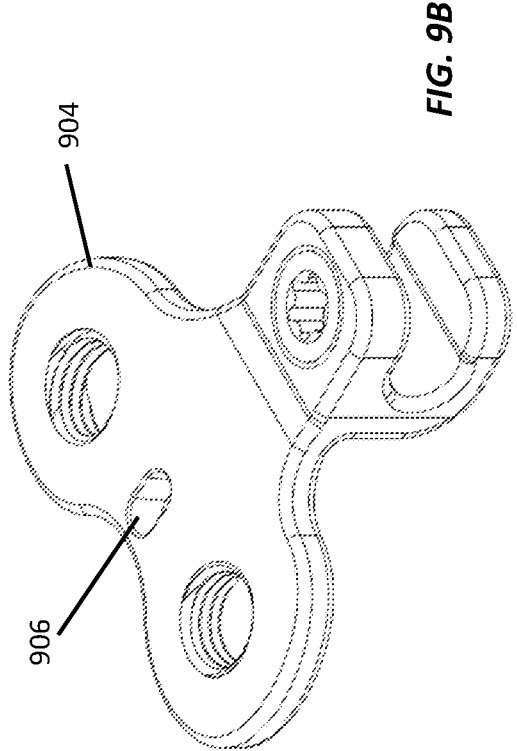
FIGS. 9A and 9B illustrate an exemplary embodiment of a rib plate consistent with the principles of the present disclosure.
Figure 9A:
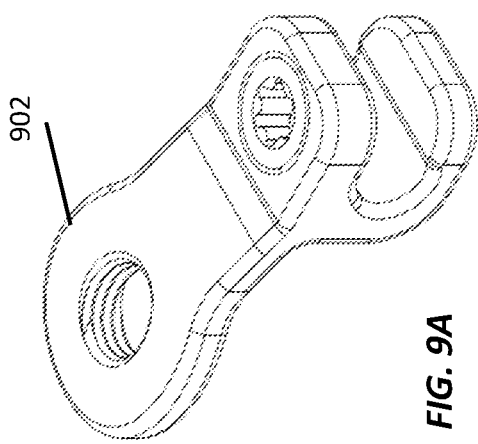

Rib plates 302, 304 connect to a longitudinal member to create stabilization of a fracture or osteotomy. The connections may be made using a set screw received in holes 314 and 316. The rib plate may have one or multiple screws or fixation points for connection to the bone. Rib plate 302 is shown with one fixation point and rib plate 304 is shown with multiple fixation points. An example of usage for the single set screw embodiment of rib plate 302 is to secure a fragment or portion of bone which has been resected or separated from the remainder of the rib, and to hold it in a certain location to function as a graft to reduce the necessary span of bone regrowth. Other related rib plates are illustrated in FIGS. 9A and 9B, showing rib plates 902 and 904.

FIGS. 4A-4F show illustrations of a polyaxial rib head anchor 400. Rib head anchor 400 may be implanted within the rib, preferably by driving a screw 402 through the longitudinal/intramedullary axis of the rib. Rib head anchor 400 may be used anywhere in the rib, but likely provides the most utility when implanted in the most proximal portion of the rib, adjacent to the transverse process, after an osteotomy is performed to remove a portion of the rib.

Rib head anchor 400 uses screw 402 assembled with a main body 404 which includes a longitudinal member 406 and a locking mechanism 408. Screw 402 may be preassembled with main body 404 or assembled at the time of the procedure. Locking mechanism 408 is shown as a set screw, but other locking mechanisms may be used.

Rib head anchor 400 is polyaxial allowing variability in angulation and rotation of rib head anchor 400 to accommodate a patient's anatomy and surgical needs. Rib head anchor 400 may be locked by various means, including but not limited to, direct friction, interlocking surfaces, or activation of a clamp or other locking mechanism.

FIGS. 5A and 5B illustrate a fixed rib head anchor 500 having a screw 502, a main body 504 which includes a longitudinal member 506. Rib head anchor 500 is similar to rib head anchor 400 but does not incorporate an adjustable polyaxial mechanism. Rib head anchor 500 is fixed to the rib using a screw 502. Screw 502 and main body 504 incorporate an interlocking mechanism which is activated by seating screw 502 into main body 504. Two examples of a possible interlocking mechanism are monoaxial and polyaxial locking holes.

FIG. 6 illustrates a splint plate 600 consistent with the principles of the present disclosure. Splint plate 600 includes a plate portion 602 and a longitudinal member 604. Plate portion 602 may be integrated with longitudinal member 604, for the creation of interconnections between implants, such as implants disclosed herein. Splint plate 600 may include one or more fixation points for connection to the surface of the rib, using bone screws or some other means.

FIGS. 7A-7C illustrate an exemplary polyaxial rib head anchor 700 consistent with the principles of the present disclosure. Rib head anchor 700 may include a bone screw 702, a clamp body 704, a flexible collet 706, and a locking nut 708. Rib head anchor may connect to a longitudinal member 710 as shown in FIG. 7D. Rib head anchor may be used anywhere in the rib including the most proximal portion of the rib, adjacent to the transverse process, after an osteotomy is performed to remove a portion of the rib.

Bone screw 702 may be implanted within the rib, preferably within the longitudinal/intramedullary axis of the rib. Bone screw 702 may include bone threads at a distal tip, a male locking spline in the midsection, and a locking thread at the proximal end, with a driving feature which may mates with a driver for insertion. The bone threads engage with the bone, and the locking spline is left exposed.

Clamp body 704 consists of a split design, in which a flexible collet 706 is assembled. Flexible collet 706 may be spherical and mate into an internal pocket of clamp body 704 of similar size. Collet 706 may be free to rotate in the neutral state of clamp body 704. At the opposite end of clamp body 704 from collet 706 are two through holes which are intended to accept the proximal locking thread geometry of bone screw 702. One of the through holes on clamp body 704 may contain a female locking spline geometry which corresponds to that of bone screw 702. It is noted that while a female locking spline on the clamp body and a corresponding male locking spline on the bone screw are disclosed, this engagement may use other types of mating geometries such as grooves, tapers, or other mating surfaces. When clamp body 704 is placed over bone screw 702 a post 712 of bone screw 702 and the locking splines are engaged, clamp body 704 and bone screw 702 become rotationally linked.

Flexible collet 706 may include a central through hole which may accept longitudinal member 712, such as a round rod, as shown in FIG. 7D. Collet 706 may contain flexures which enable the application of a clamping force to longitudinal member 712. The outer surface of collet 706 may be textured or have locking geometry, which may mate with corresponding textured or locking geometry on clamp body 704.

When longitudinal member 712 is placed into collet 706, and clamp body 704 and collet 706 are placed onto bone screw 702 which has been implanted into the bone, longitudinal member 712 and collet 706 may rotate through a certain range of motion within clamp body 704, enabling assembly of a construct to span an osteotomy or fracture. Locking nut 708 may be introduced to constrain this motion, by engaging with locking threads of bone screw 702, and applying force to the split portion of the clamp body 704. This force causes clamp body 704 to flex and close, and the resulting action provides a clamping force to collet 706, which in turn provides a clamping force to longitudinal member 712.

FIGS. 8A and 8B illustrate a rib head anchor system 800 consistent with the principles of the present disclosure. Rib head anchor system 800 is similar to rib head anchor 700 but in place of the bone screw which engages the intramedullary space of the bone, a plate 802 allows for attachment to the outer surface of bony anatomy. The outer surface may be either the outer surface of the rib or the outer surface of the transverse process.

Figure 10C:
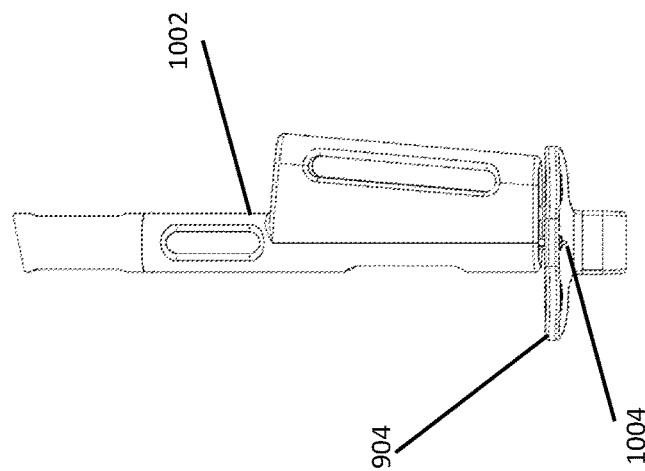
FIGS. 10A-10C illustrate an exemplary embodiment of a rib plate and a screw guide for fixating the plate to a bone consistent with the principles of the present disclosure.
Figure 10B:
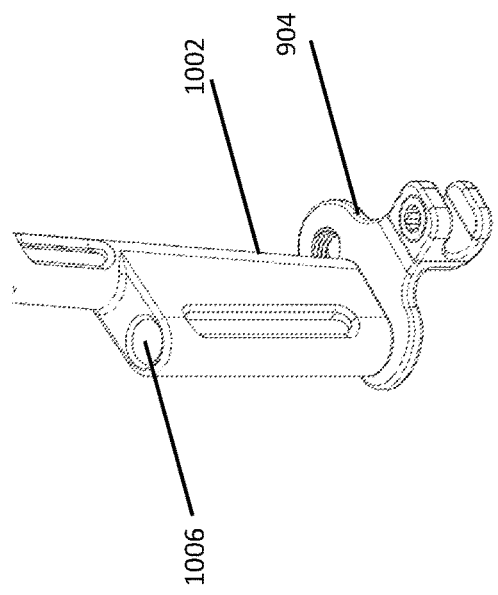
Figure 10A:
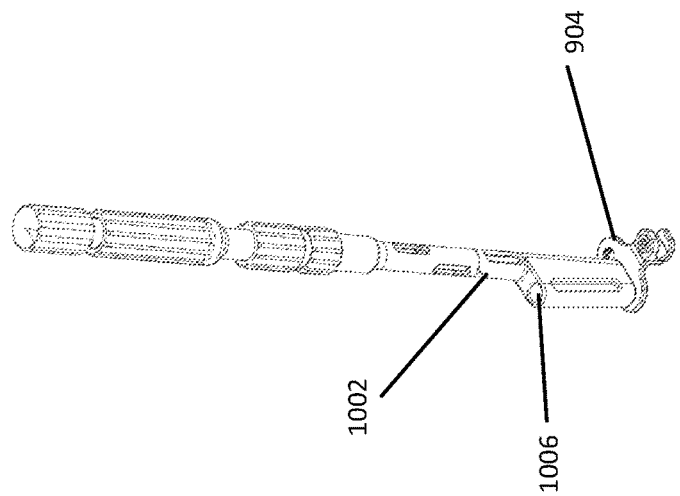

FIGS. 10A-10C illustrates screw guide 1002 consistent with principles of the present disclosure. Screw guide 1002 may be used for plates having a dual screw configuration such as plate 904 shown in FIG. 9B. Plate may have a mating feature 906 to attach to screw guide 1002 to facilitate attachment of plate 904 to bone. Mating feature 904 may be a female slot on the plate that engages with an expanding, split male feature 1004 on screw guide 1002 (shown in FIG. 10C).

Screw guide 1002 may allow the user to position and hold a plate in place while helping to align the appropriate instruments for insertion of the locking bone screw, which is shown in FIGS. 10A-10C in a converging trajectory. A cannula 1006 is provided at the distal end of screw guide 1002 which allows coaxial alignment with screw holes in the plate. The user may use a drill and/or awl to prepare the pathway for the locking bone screw via cannula 1006, and then pass the bone screw which is attached to a driver. After placement of one screw, cannula 1006 may be rotated about the central axis to align with the opposite locking bone screw trajectory for insertion.

Figure 11B:
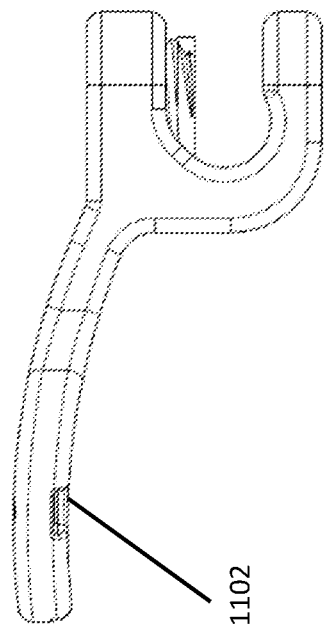
FIGS. 11A and 11B illustrate an exemplary embodiment of a rib plate consistent with the principles of the present disclosure.
Figure 11A:
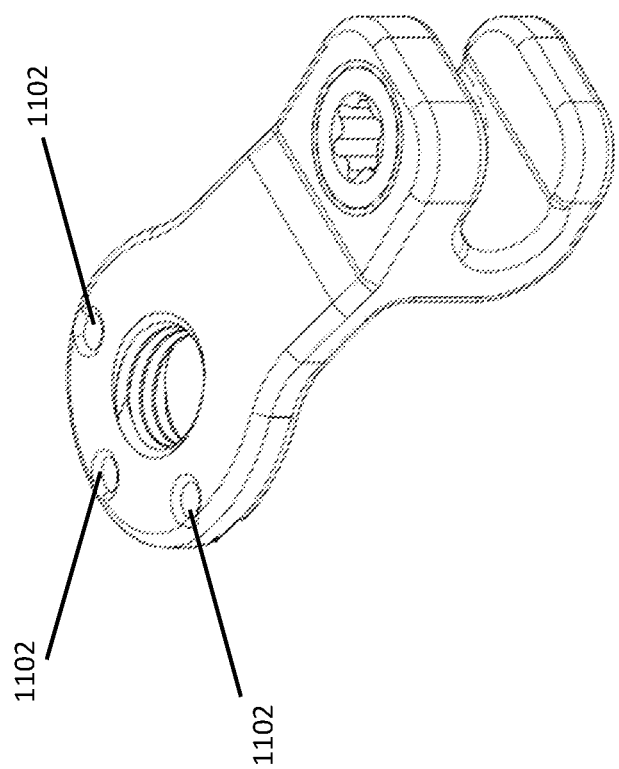

Referring to FIGS. 11A and 11B, the plates described herein may include suture holes 1102 to facilitate attachment of soft tissue to the plate or provide additional support to secure the implant to bony anatomy.

Figure 12B:
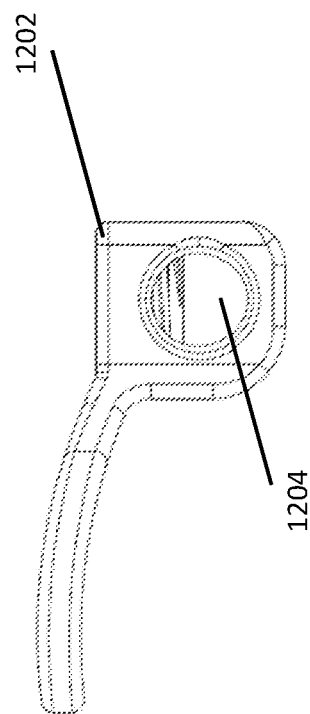
FIGS. 12A and 12B illustrate an exemplary embodiment of a rib plate consistent with the principles of the present disclosure.
Figure 12A:
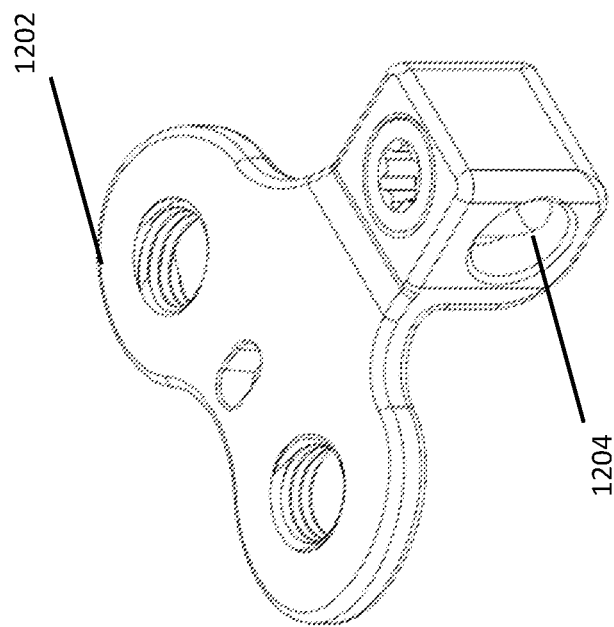

Referring to FIGS. 12A and 12B, illustrated is a plate 1202 in a closed configuration. Any of the plates described herein may be configured in a closed configuration, where a longitudinal member is passed through a clamp portion 1204 of the plate. This may provide additional stability by reducing the potential for the longitudinal member to escape the clamp during manipulation and correction of an osteotomy or fracture.

Figure 13B:
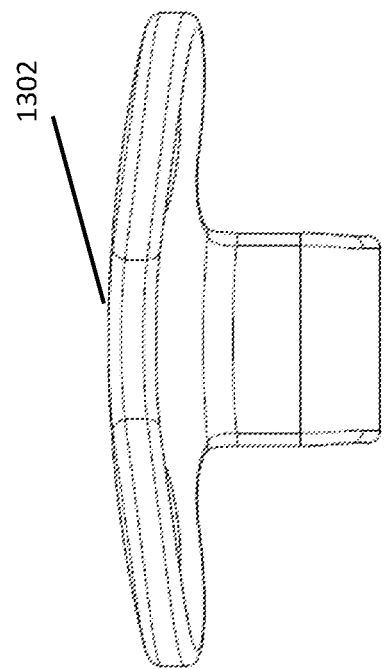
FIGS. 13A and 13B illustrate an exemplary embodiment of a rib head anchor consistent with the principles of the present disclosure.
Figure 13A:
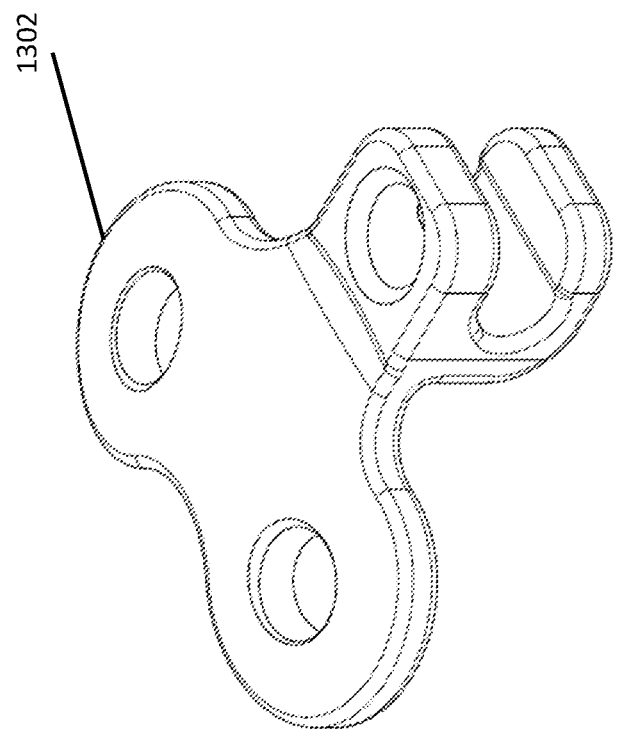
Figure 14E:
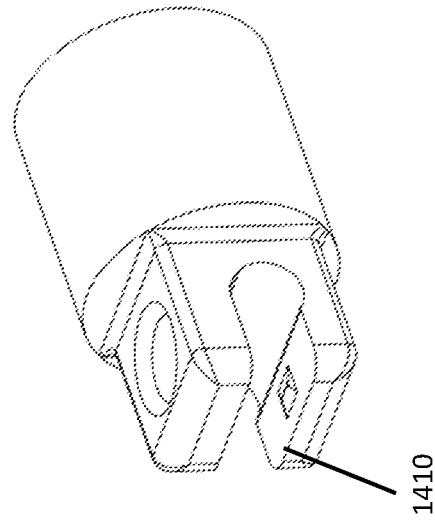
Figure 14G:
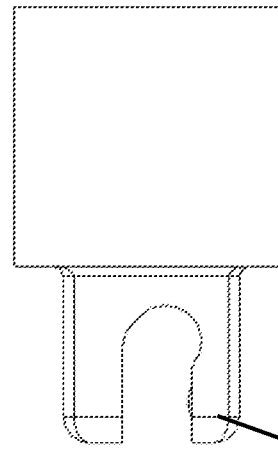
Figure 14F:
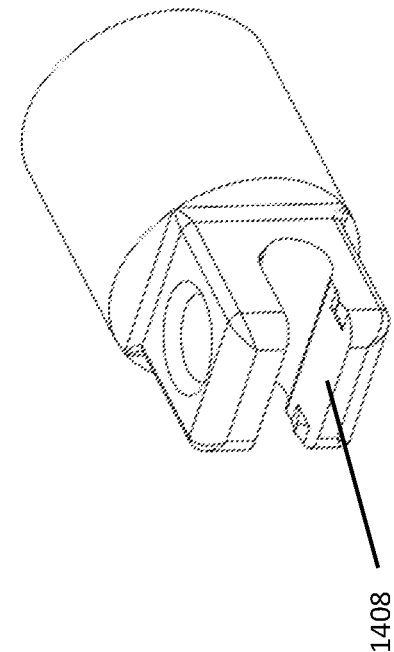
Figure 14H:
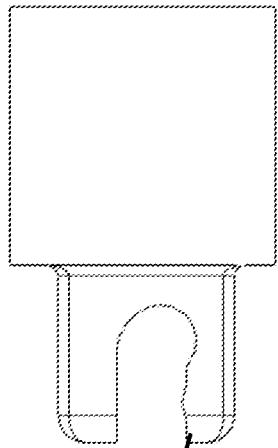

Illustrated in FIGS. 13A and 13B, a plate 1302 may be curved in multiple planes to better accommodate complex geometry of the ribs. Plate 1302 is configured such that a portion of the plate is contoured in both the cephalad-caudal and proximal-distal planes of the rib.

FIGS. 14A-H illustrate provisional capture features 1402 and 1404. FIG. 13B shows a side view of FIG. 13A and FIG. 13D shows a side view of FIG. 13C. This may apply to any of the clamps for plates described herein. The plates may be augmented with the provisional capture features 1404, 1406, which provides tactile and/or audible feedback to the user to indicate that the longitudinal member has been provisionally captured in the clamp. The performance of the provisional capture features 1404, 1406 is accomplished by allowing a portion of the device to flex and allow passage of the longitudinal member.

FIGS. 14A-14D illustrate provisional capture features 1404, 1406. Provisional capture features 1408, 1410 is accomplished by interfering geometry located within the clamp mouth. The magnitude of the interference will be appropriately small such that the longitudinal member may be seated into the clamp by applying force by hand or with an instrument. The interference features may be located on opposing surfaces within the clamp mouth, or may be one-sided, opposing only the normal clamp geometry.

FIGS. 15A-15C illustrate monoaxial locking bone screws for rib plates consistent with the principles of the present disclosure. Screw 1502 may be a self-tapping screw and screw 1504 may be a self-drilling screw. These bone screws may be used with any of the plates described herein to secure the plate to the bony anatomy of the rib surface.

Bone screw 1502 includes a self-tapping configuration having three (3) swept cutting flutes at the distal end. Bone screw 1504 includes a self-drilling configuration having a sharp tip. Both configurations have bone threads at the distal end, with a tapered monoaxial locking head at the proximal end as well as a female drive feature (for example, a hexalobe).

The monoaxial locking geometry may be of a dual-lead tapered thread form, with the male/external thread geometry on the screw head, and the female/internal thread geometry on the corresponding hole on the plate device. Locking is accomplished by driving the screw through the corresponding hole on the plate, causing engagement of the tapered threads and eventual interference of the thread geometry.

Illustrated in FIGS. 16A and 16B are rib plates 1602 and 1604 consistent with the principles of the present disclosure. Plates 1602 and 1604 may be disposed on the bony surface of the rib and span a fracture or osteotomy. The plate consists of several locking hole features 1606, 1608 along the length of the plate for fixation onto the rib. Holes 1604, 1606 may have the same monoaxial tapered locking geometry as described above. Plates 1602, 1604 may have a scalloped design to facilitate bending in multiple planes. The plates may also include k-wire holes and/or suture holes 1610, 1612. The bottom surface of the plate may be contoured in the cephalad-caudal plane to match the anatomy of the rib, or it may be flat. The plate may be configured in a straight, unbent configuration (FIG. 16A) or a precontoured configuration (FIG. 16B).

Referring now to FIGS. 17A-17C, illustrated is a splint plate 1702 consistent with the principles of the present disclosure. Here, splint plate 1702 is similar to splint plate 600 of FIGS. 6A and 6B. Splint plate 1702 may include a longitudinal member that is pre-contoured to reduce the amount of bending required by the user during surgery.

Advantages of the above concepts include better fixation of rib fractures and osteotomies, with preference to treatment of osteotomies. The rib head anchors enable fixation in ribs which have been resected close to the transverse process, which would be challenging to fixate using conventional trauma plating methods. Similarly, the low profile of the splint plates allow fixation near a rib head.

The concepts and described here offer significant advantages in treating deformities of the proximal ribs, such as rib hump, but also may be useful in the correction of general chest wall and rib deformities. The symmetric longitudinal member allows contouring in any or multiple planes to achieve a desired outcome. Such contouring is challenging using traditional trauma-plating type devices. The longitudinal member also allows for compression and distraction along the length of the rib to facilitate fracture reduction or direct chest wall expansion. Similarly, the modular nature of the devices described here allows the use of any of multiple techniques, to accommodate the specific surgical needs of the doctor and the anatomy of the patient.

These and other advantages of the present disclosure will be apparent to those skilled in the art from the foregoing specification. Accordingly, it will be recognized by those skilled in the art that changes or modifications may be made to the above-described embodiments without departing from the broad inventive concepts. It should therefore be understood that this disclosure is not limited to the particular embodiments described herein, but is intended to include all changes and modifications that are within the scope and spirit of the disclosure as defined in the claims.

What is claimed is:

1. A rib plate for treating a fracture of a rib bone, the rib plate defining a first horizontal plane and a second horizontal plane, comprising:
   a plate portion configured to contact a surface of the rib bone to be treated;
   a first screw hole configured to receive a first screw to fixate the plate portion to the surface of the rib bone to be treated, the first screw hole positioned on the first horizontal plane;
   an implant portion having a hole positioned on the second horizontal plane and a channel configured to receive a longitudinal member; and
   a fastener received in the hole to secure the longitudinal member to the implant portion, wherein the first horizontal plane is positioned vertically above the second horizontal plane, and
   wherein the first horizontal plane and the second horizontal plane are positioned above the channel configured to receive the longitudinal member.

2. The rib plate of claim 1, further comprising a second screw hole to receive a second screw to fixate the plate portion to the surface of the rib bone to be treated.

3. The rib plate of claim 1, wherein the implant portion is configured to receive the longitudinal member in a top-loading manner on a top surface of the rib plate.

4. The rib plate of claim 1, wherein the longitudinal member is secured in the implant portion via the fastener which is a set screw.

5. The rib plate of claim 1, wherein the implant portion is configured to receive the longitudinal member in a side-loading configuration.

6. The rib plate of claim 1, further comprising a second screw hole to receive a second screw, wherein the plate portion contains a mating feature to attach to a screw guide.

7. The rib plate of claim 6, wherein the mating feature is disposed between the first screw hole and the second screw hole.

8. The rib plate of claim 1, wherein the plate portion is contoured in a cephalad-caudal plane and a proximal-distal plane.

9. The rib plate of claim 1, wherein the plate portion includes one or more suture holes for aiding in fixation to soft tissue around the rib bone to be treated.

10. The rib plate of claim 1, wherein the implant portion is a clamp configured to receive the longitudinal member.

11. A rib plate system for treating a fracture of a rib bone, comprising:
    a rib plate configured to contact a surface of the rib bone, the rib plate defining a first horizontal plane and a second horizontal plane, comprising:
        a plate portion configured to contact a surface of the rib bone to be treated;
        a first screw hole, the first screw hole positioned on the first horizontal plane; and
        an implant portion having a channel and a hole positioned on the second horizontal plane and,
    a first screw configured to be received in the first screw hole to fixate the rib plate to the rib bone;
    a longitudinal member configured to attach to the implant portion,
    a fastener received in the hole to secure the longitudinal member to the implant portion,
    wherein the first horizontal plane is positioned vertically above the second horizontal plane,
    wherein the first horizontal plane and the second horizontal plane are positioned above the channel configured to receive the longitudinal member.

12. The rib plate system of claim 11, further comprising a second screw and wherein the rib plate includes a second screw hole to receive the second screw to fixate the rib plate to the rib bone.

13. The rib plate system of claim 11, wherein the implant portion is configured to receive the longitudinal member in a top-loading manner on a top surface of the rib plate.

14. The rib plate system of claim 11, wherein the fastener is a set screw.

15. The rib plate system of claim 11, wherein the implant portion is configured to receive the longitudinal member in a side-loading configuration.

16. The rib plate system of claim 11, further comprising a second screw hole to receive a second screw, wherein the plate portion contains a mating feature to attach to a screw guide.

17. The rib plate system of claim 16, wherein the mating feature is disposed between the first screw hole and the second screw hole.

18. The rib plate system of claim 11, wherein the plate portion is contoured in a cephalad-caudal plane and a proximal-distal plane.

19. The rib plate system of claim 11, wherein the plate portion includes one or more suture holes for aiding in fixation to soft tissue around the rib bone to be treated.

20. The rib plate system of claim 11, wherein the implant portion is a clamp configured to receive the longitudinal member.

* * * * *